United States Patent [19]

Lubitz et al.

[11] 4,277,977
[45] Jul. 14, 1981

[54] METHOD AND APPARATUS FOR INSPECTION OF CERAMIC PARTS FOR DEFECTS

[75] Inventors: Karl Lubitz, Ottobrunn; Jeffrey M. Drew; Werner P. Schuhmann, both of Munich, all of Fed. Rep. of Germany

[73] Assignee: Siemens Aktiengesellschaft, Berlin & Munich, Fed. Rep. of Germany

[21] Appl. No.: 47,476

[22] Filed: Jun. 11, 1979

[30] Foreign Application Priority Data

Aug. 8, 1978 [DE] Fed. Rep. of Germany ....... 2834695

[51] Int. Cl.³ ............................................ G01N 29/00
[52] U.S. Cl. ...................................................... 73/587
[58] Field of Search .......................... 73/587, 649, 658

[56] References Cited

U.S. PATENT DOCUMENTS 3,924,456  12/1975  Vahaviolos ............................ 73/587

OTHER PUBLICATIONS

A. G. Evans et al.; "Failure Prediction in Structural Ceramics", *Materials Evaluation*, pp. 85-96, Apr. 1977.
J. E. Garnier et al.; "Applications of Acoustic Emission to Evaluation of Dielectric Breakdown in Insulator Materials", American Ceramic Society Bulletin, vol. 55 No. 5, pp. 553-554, May 1976.

*Primary Examiner*—Stephen A. Kreitman
*Attorney, Agent, or Firm*—Hill, Van Santen, Steadman, Chiara & Simpson

[57] ABSTRACT

A method and apparatus for inspection of ceramic parts for defects utilizes the application of an electrical test voltage to the part to be inspected, and at the same time subjecting the part to acoustic emission analysis. Use of the acoustic emission analysis allows discovery of not only defects which may arise because of the application of the electric current, but also defects or structural damage which are already existant in the part to be tested. An apparatus for carrying out the method on a high-volume basis allows rapid insertion and removal of a part between electrodes and clamps the part in place during testing.

6 Claims, 4 Drawing Figures

METHOD AND APPARATUS FOR INSPECTION OF CERAMIC PARTS FOR DEFECTS

BACKGROUND OF THE INVENTION

1. Field of the Invention

The present invention relates to a method and apparatus for the inspection of ceramic parts for structural and electrical defects therein, and, in particular for the inspection of posistors under electric loading.

2. Description of the Prior Art

Ceramic structural members, such as power posistors must possess a certain resistance to switching transients. Generally, a customer prescribes a specific switching arrangement and testing voltage and requires that the posistor survive a high number of switchings under these conditions without damage to the part.

Conventional methods of testing posistors apply a switching voltage to the posistor and the resistance of the posistor is measured before and after the application of voltage. If the resistance is increased after the application, it is assumed that mechanical defects were generated in the posistor during the electrical loading or that pre-existing defects were magnified thereby. This method has the disadvantage that minute defects which may lead to a gradual destruction of the part after a large number of switchings under testing voltage are not revealed. This is beause such minute defects will not measurably alter the electrical characteristics of the posistor, which will appear normal despite the presence of such minute defects. Only after a repeated number of switchings do such minute defects increase to a point such that an immediate destruction of the ceramic during switching occurs, or gradual destruction of the part occurs.

Some methods for inspecting for mechanical defects are known which utilize ultrasonics. Such processes still provide no definitive information as to the resistance of a particular part to switching transients because of the natural porosity of the ceramic and, again, because of the ofter minute extent of the defects. The same is true for currently employed electrical attenuation measurements, with which good results can be attained only in special cases.

All of the above methods also have the common disadvantage that detection of only mechanical defects is possible thereby. The greater number of switching failures is caused by resistance inhomogeneities in a mechanically fault-free ceramic part.

SUMMARY OF THE INVENTION

In accordance with the principles of the present invention inspection of directly ceramic parts such as posistors ensues by the application of an electrical test voltage to the part to be inspected and simultaneously subjecting the part to acoustic emission analysis. The latter analysis supplies information concerning the material structure, and reveals any damage that may occur as a result of the application of the electric voltage or due to an already existing structural fault in the material.

By applying a one-time excess electric voltage, it is determined whether the part being inspected can withstand a large number of switches or normal voltage. At the same time it is determined whether or not the sample was damaged by the one-time overload. A determination can thus be made with a single test whether or not the sample will be damaged upon subjection to a permanent load of normal voltage. A long-term test at normal or specified voltages can thus be eliminated. The presence of a pre-existing mechanical structural fault in the posistor can also be determined by the sound emission analysis. Immediately upon application of a voltage to the posistor, the ceramic material heats unevenly in the area of the structural damage, because the homogenous current flow is disrupted at that point. The fissure surfaces rub against one another and generate acoustic or sound pulses even if the fissure does not expand.

Sound pulses are generated, however, even when the sample is in thermal equilibrium with no expansion of the mechanical defect. The electrical contact resistance from fissure surface to fissure surface increases as the surfaces are pressed more strongly against each other, which occurs to a greater degree with higher temperatures. As the contact resistance decreases, the electrical self-heating drops and thus the temperature in the area of the fissure and the contact pressure of the fissure surfaces also decreases. Temperature oscillations arise in the area of the pre-existing damage which generates acoustic or sound pulses by the rubbing together of the fissure surfaces for as long as the electric voltage is applied to the posistor.

This method is most advantageously employed when the acoustic measurement is activated immediately after the voltage is switched on. Transient electric pulses arising as a result of the switching on of the voltage may simulate sound pulses because of the electrical coupling in some amplifier units, and thus produce erroneous data. Such error is eliminated when sound measurement takes place only after activation of the voltage.

An apparatus for the implementation of the above method has sound pick-ups which are biased against the surface of the part to be inspected, which is clamped between two leaf-spring electric contacts. A quick interchange of parts to be inspected is thus facilitated.

Further, the apparatus is designed so that all parts of the support mounting can be easily turned and all points contacting a part to be inspected may be coated with a quick-release synthetic resin, such as "Teflon." Interference noise pulses which could conceivably arise because of friction between the quickly heating and expanding part and the support mounting are suppressed.

It is thus an object of the present invention to inspect ceramic parts such as posistors by means of the simultaneous employment of electrical loading and sound emission analysis.

It is a further object of the present invention to provide such an inspection means which has the ability to determine the existance of minute defects which may lead to a gradual destruction of the posistor after a large number of switching loads.

Another object of the present inventions is to provide an apparatus for implementing the above method which facilitates quick interchange of parts, thereby allowing inspection of a high volume of parts.

DESCRIPTION OF THE PREFERRED EMBODIMENTS

Figure 1:
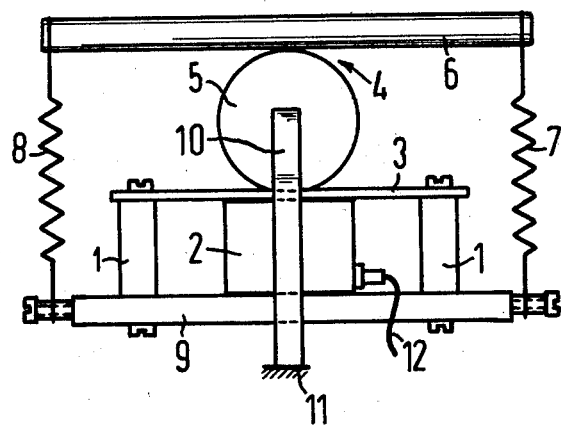
FIG. 1 is a schematic illustration of an apparatus for the inspection of ceramic parts such as posistors for defects.

An apparatus for the inspection of ceramic parts for defects is schematically shown in FIG. 1. The apparatus consists of a base plate 9 having two upwardly extending probe supports 1 attached thereto. The probe supports 1 support a teflon plate 3 generally parallel to the base plate 9.

An acoustic probe 2 of conventional construction is disposed between the base plate 9 and the teflon plate 3. An output 12 leads to conventional analyzing and display circuitry (not shown).

A posistor 4 having an end contact or electrode 5 rests on the teflon plate 3. A round teflon bar 6 is biased against the posistor 4 by tension springs 7 and 8.

Electric current is supplied to the posistor 4 by means of terminals 10 (only one of which is shown) at each end terminal 5 of the posistor 4. The terminal 10 is connected to a power source 11.

Figure 2:
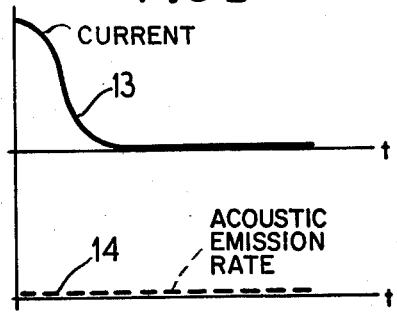
FIGS. 2 through 4 are temporal graphic representations of current and sound outputs obtained for various posistors inspected in the device of FIG. 1.
Figure 4:
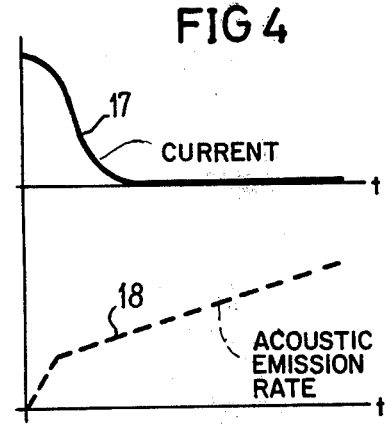
Figure 3:
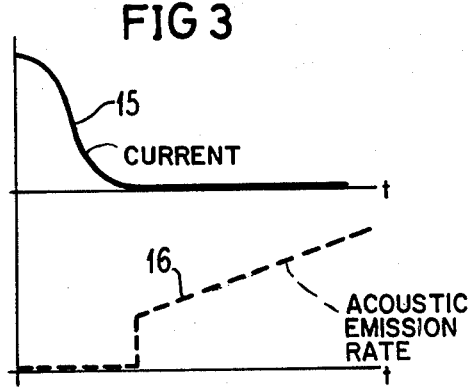

Current and acoustic outputs for various posistors tested in the device of FIG. 1 are graphically represented in FIGS. 2 through 4. In all Figures, the upper solid line represents current output and the dashed lower line represents acoustic output. Time t is measured on the abscissa.

Current and sound outputs for a posistor having no defects are shown in FIG. 2. As represented by the curve 13, the current sinks after a specific time as is usual in posistors after application of a voltage. The substantially flat sound output 14 shows that not only were there no pre-existing defects in the inspected part, but also that no defects were produced by application of voltage.

The acoustic output curve 16 shown in FIG. 3 is characteristic of an inspected part which exhibited no pre-existing damage, but to which damage occurred by the application of a high voltage, shown by the sharp vertical discontinuity in the curve 16.

It will be noted that the current output curve 15 still appears normal.

The curves of FIG. 4 are representative of an inspected part had pre-existing damage thereto, as evidenced by the acoustic curve 18 which immediately begins to rise. Again, the current output 17 appears normal.

Although changes and modifications may be suggested by those skilled in the art it is the intention of the inventors to embody within the patent warranted hereon all changes and modifications as reasonably and properly come within the scope of their contribution to the art.

We claim as our invention:

1. A method for inspection of semiconductor ceramic structural members for defects therein comprising the steps of:
   applying a test voltage to the member to be inspected, and
   simultaneously subjecting the member to acoustic emission analysis
   whereby structural damage resulting from the application of said test voltage, and the presence of pre-existing damage are determined by examination of acoustic pulse output.

2. The method of claim 1 wherein said test voltage is applied before said member is subjected to said acoustic emission analysis, said test voltage being maintained during said acoustic emission analysis.

3. A method for the inspection of semiconductor ceramic structural members for defects therein comprising the steps of:
   inserting a part to be inspected between two electrodes contacting electric terminals of said part;
   clamping said part to be inspected against an acoustic probe of an acoustic emission analysis system;
   applying a test voltage to said part through said terminals;
   maintaining said test voltage while subjecting the part to acoustic emission analysis;
   releasing said part from said contacts and from said acoustic probe; and
   examining the acoustic pulse output of said acoustic emission analysis to determine whether said part has been damaged by the application of said test voltage and whether pre-existing damage to said part is present.

4. A device for inspecting semiconductor ceramic structural members for defects therein comprising:
   a base;
   an acoustic probe supported above and parallel to said base;
   a means connected to said acoustic probe for displaying acoustic pulses under test conditions of applied voltage;
   a means for applying a test voltage to said ceramic structural member;
   a means for clampingly holding said ceramic structural member against said acoustic probe,
   whereby sai- ceramic structural member is simultaneously subjected to said test voltage and acoustic emission analysis to determine structural damage caused by the application of said test voltage and the presence of pre-existing structural damage.

5. The device of claim 4 wherein said means for clampingly holding said ceramic structural member against said acoustic probe is a bar horizontally disposed above and parallel to said acoustic probe and biased for normal movement toward siad acoustic probe by a plurality of tension springs perpendicularly interconnected between said base and said bar.

6. The device of claim 4 wherein said acoustic probe and said means for clampingly holding said ceramic structural member against said acoustic probe are coated with polyfluoroethylene to facilitate rapid insertion and removal said structural member, and to minimize transient pulses generated by frictional engagement of said ceramic structural member and said device.

* * * * *